United States Patent [19]

Pecht et al.

[11] Patent Number: 4,996,296
[45] Date of Patent: Feb. 26, 1991

[54] CROMOLYN BINDING PROTEIN IN HIGHLY PURIFED FORM, AND METHODS FOR THE ISOLATION THEREOF

[75] Inventors: Israel Pecht, Rehovot, Israel; Stefan Hemmerich, Konstanz, Fed. Rep. of Germany

[73] Assignee: Yeda Research & Development Co., Ltd., Rehovot, Israel

[21] Appl. No.: 78,134

[22] Filed: Jul. 27, 1987

Related U.S. Application Data

[63] Continuation-in-part of Ser. No. 843,912, Mar. 20, 1986; Pat. No. 4,683,135, which is a continuation of Ser. No. 517,843, Jul. 27, 1983, abandoned.

[51] Int. Cl.$^5$ .................. C07K 15/06; C07K 3/20; C07K 15/14
[52] U.S. Cl. .................. 530/350; 530/413; 530/395; 530/380; 530/830; 530/802
[58] Field of Search ............... 530/350, 387, 380, 395, 530/400, 4

[56] References Cited

U.S. PATENT DOCUMENTS 4,683,135  7/1987  Pecht et al. .................. 530/350

OTHER PUBLICATIONS

Mazurek et al., EMBO J., 1(5), 585–90, (1982).
Mazurek et al., PNAS, 80, 6014–18, (1983(Oct.)).
Mazurek et al., PNAS, 81, 6841–5, (Nov. 1984).

*Primary Examiner*—Garnette Draper
*Assistant Examiner*—Jeff Kushan
*Attorney, Agent, or Firm*—Browdy and Neimark

[57] ABSTRACT

Substantially pure cromolyn binding protein is prepared by means of affinity chromatography of cromolyn derivatives bound to insoluble matrices. Aminocromolyn is prepared by a six-step synthesis and amine derivatives thereof are prepared by conventional means. Obtaining a compound having an amine group instead of the OH group at the 2-carbon of the propane link of cromolyn permits many kinds of reactions without interfering with the portion of the cromolyn molecule with causes its pharmacological activity. The cromolyn derivatives can be conjugated to proteins such as BSA by means of glutaraldehyde cross-linking and such conjugates can be covalently bound to agarose beads. Cromolyn binding protein can be isolated by passing lysates of RBL-2H3 cells through chromatographic columns packed with such beads. The cromolyn binding protein can be further purified by means of lectin-agarose columns.

10 Claims, 9 Drawing Sheets

FIG.5

```
        WGA                        Con A
  ┌──────────────┐          ┌──────────────┐
  2  3 E2 E3 E4 E5 E6 B     2  3 E2 E3 E4 E5 E6  B
```

$Mr \times 10^{-3}$

—93—

—67—

—43—

—30—

—20.1—

—14.4—

CROMOLYN BINDING PROTEIN IN HIGHLY PURIFED FORM, AND METHODS FOR THE ISOLATION THEREOF

CROSS REFERENCE TO RELATED APPLICATION

This application is a continuation-in-part of United States application Ser. No. 843,912 filed Mar. 20, 1986, now Pat. No. 4,683,135, which was a continuation of application Ser. No. 517,843, filed July 27, 1983, now abandoned, the entire contents of both of which are hereby incorporated by reference.

FIELD OF THE INVENTION

The present invention relates to processes for the preparation of a chemically substantially pure membrane component of basophils and mast cells capable of binding $Ca^{2+}$-ions and the anti-allergic drug cromolyn, as well as to the purified protein itself. This protein will hereinafter be referred to as "cromolyn binding protein" or "CBP." The present invention also relates to novel derivatives of cromolyn and to the production thereof as well as to poly-cromolyn derivatives and to insoluble matrices in which the novel cromolyn derivatives have been chemically bonded for use in isolating cromolyn binding protein, as well as to binding assays and affinity chromatography for the production of highly purified cromolyn binding protein.

BACKGROUND OF THE INVENTION

Immediate hypersensitivity (allergy) has been shown to be mediated by a distinct class of immunoglobulins, namely IgE. This antibody binds via its Fc-domains to specific high affinity receptors on the surface of mast cells and basophils. Upon binding of the receptor bound IgE to the polyvalent antigen (the allergen), the IgE-receptors are cross-linked, providing a signal by which the cell is triggered to release histamine and serotonin from their granules into the extracellular space. These compounds are responsible for the pathologic manifestations of allergy (Ishizaka et al., *Proc. Natl. Acad. Sci. (U.S.A.)*, 76:5858 (1979), c.f. Ishizaka, T. et al, *Prog. Allerg.*, 34: 188 (1984)).

The nature and sequence of biochemical processes which couple the IgE-mediated stimulus to mediator secretion from mast cells are topics of considerable research interest and activity. One of the different early events which has been most intensively examined and discussed, is the transient increase in the concentration of free $Ca^{2+}$-ions in the cytosol ($[Ca^{2+}]_i$) of mast cells of different origins. The requirement of millimolar concentrations of $Ca^{2+}$ in the extracellular medium for the immunologically triggered secretion has been widely documented and was interpreted to reflect a net influx of these ions into cells, via ion channels, flowing down their concentration gradient. In recent years the discovery of the capacity of inositol triphosphate to release sequestered $Ca^{2+}$-ions from intracellular depots led several investigators to propose, that the source of the transient rise in $[Ca^{2+}]_i$ is intrinsic rather than due to a channel mediated influx. IgE-mediated secretion and examination of these ions' influx with $^{45}Ca^{2+}$ as tracer further supported the notion of a channel opening being the main force of the rise in $[Ca^{2+}]_i$.

Cromolyn has been introduced as a therapeutic drug for allergic asthma under the names Ital and Lomudal (Cox et al., *Adv. in Drug Res.*, 5:115-195 (1970)). Cromolyn is the disodium salt of 1,3-bis-(2-carboxychromone-5'-yloxy)-2-hydroxypropane and is also known as disodium cromoglycate and DSCG. Throughout the present specification and claims, this drug will be referred to as "cromolyn." Whereas many antiallergic drugs exert their effect distal to the histamine release, cromolyn is believed to interface with the mechanism leading to a transiently elevated $[Ca^{2+}]_i$ upon antigenic stimulation of the cell. Hence, it prevents the secretion from taking place. In mast cells cromolyn has been shown to inhibit the degranulation and the antigen-induced $^{45}Ca^{2+}$-influx to a certain degree (Cox, *Nature*, 216:1328 (1967); Mazurek, et al., *Nature*, 303:528 (1983)). This led to the idea that the drug may interact with a certain membranal component, which is involved in the receptor-mediated calcium influx into mast cells and basophils, and has raised the possibility of isolating this component by affinity procedures based on this interaction.

Parent applications Ser. No. 843,912 and 517,843 describe the isolation of such a membrane component from mast cells and basophils. See also Mazurek et al, *Proc. Natl. Acad. Sci. U.S.A.*, 80:6014 (1984); Mazurek et al, *EMBO Journal*, 1:585-590 (1982); Pecht et al, In: *Mast Cell Differentiation and Heterogeneity*, Ed. Befus et al, Raven Press, New York, N.Y. (1986). This component was isolated using matrices assumed to be carrying cromolyn. The procedure employed in said earlier application for conjugating commercially available cromolyn to carriers involved a putative alkylation of cromolyn with the bifunctional reagent 2-aminoethane-1-sulfate to yield an amino-derivative that could be cross-linked to amine residues of proteins by glutaraldehyde. Since the date of said earlier application, it has been established that this procedure does not yield the desired conjugation. Although the matrices prepared by this procedure do yield a component, which when assayed in reconstituted lipid planar bilayers exhibits IgE-$Fc_\epsilon$-receptor gated ion channel activity, the amount of active component obtained by this process was so minute that the initial characterization thereof was not entirely accurate. This problem can be traced back predominantly to the failure in covalently conjugating the drug to its carriers.

SUMMARY OF THE INVENTION

Accordingly, it is an object of the present invention to prepare well defined cromolyn analogs which can be covalently attached to different carriers with controlled stoichiometry.

It is a further object of the present invention to prepare insolubilized conjugates of such analogs onto solid carrier materials.

It is a still further object of the present invention to use such conjugates to isolate purified cromolyn binding protein.

It is another object of the present invention to provide improved processes for obtaining substantial quantities of substantially pure cromolyn binding protein.

It is yet another object of the present invention to fully and accurately characterize the cromolyn binding protein which is obtained.

These and other objects may be accomplished in accordance with the present invention. According to the present invention, there are provided novel derivatives of cromolyn or compounds with a related chromone structure, as represented by the following Formulae I-IV

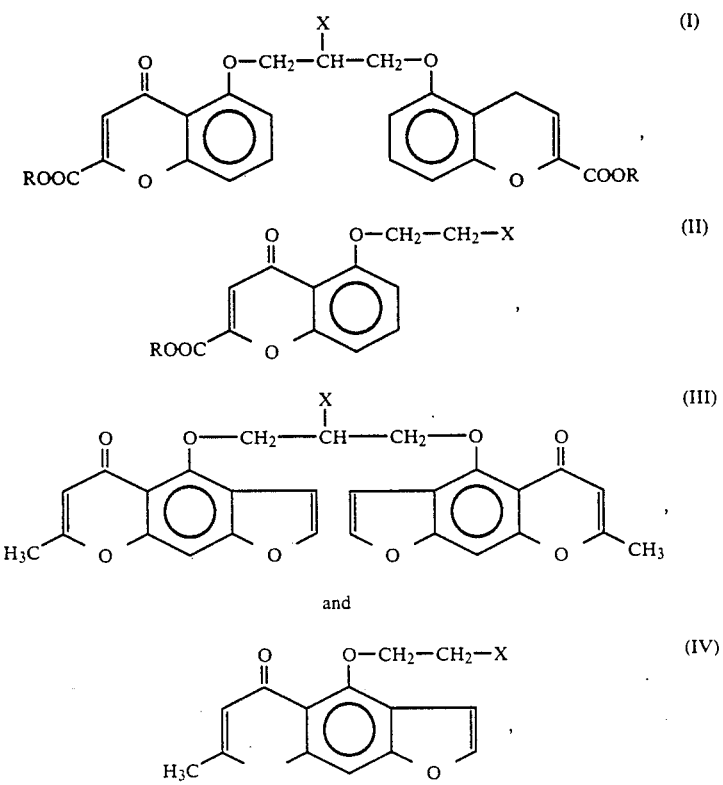

wherein R is hydrogen or $C_{1-5}$ alkyl and X is an amine or an amine derivative.

These derivatives carry an amine or an amine derivative, X, which can be used for the creation of a stable linkage to an activated carrier, biological molecules or haptens, by well established procedures, through the 2-carbon of the propane bridge to the cromolyn derivative or via an equivalent position. The amine derivative may be a chemically reactive group, a residue which serves as a substrate for a reactive group on the macromolecule or activated carrier, or on a bifunctional reagent, or it may be a hapten for which antibodies may be raised.

New and improved procedures have also been developed to effect the isolation of cromolyn binding protein (CBP) which utilize the affinity matrices bound to the cromolyn derivatives in accordance with the present invention. Additional means of purification have also been developed so that sufficient quantities of highly purified cromolyn binding protein have been prepared that an accurate amino-acid composition of this protein can be determined. It has been determined that the apparent molecular mass of the cromolyn binding protein is 110,000 in intact form or 50,000 in reduced form; both the intact and reduced form are glycosylated. The amino acid composition of the reduced form (50 kD) is given in Table I.

TABLE I

| Amino Acid | % w/w | % mol/mol |
|---|---|---|
| Asp | 9.32 | 8.78 |
| Thr | 4.20 | 4.53 |
| Ser | 5.99 | 7.43 |
| Glu | 15.37 | 12.89 |
| Gly | 6.17 | 11.71 |
| Ala | 5.31 | 8.08 |

TABLE I-continued

| Amino Acid | % w/w | % mol/mol |
|---|---|---|
| Val | 8.40 | 9.19 |
| Met | 0.99 | 0.78 |
| Ile | 6.23 | 5.96 |
| Leu | 7.47 | 7.15 |
| Tyr | 1.85 | 1.24 |
| Phe | 3.89 | 2.86 |
| His | 7.96 | 6.28 |
| Lys | 8.95 | 7.78 |
| Arg | 8.02 | 5.57 |

BRIEF DESCRIPTION OF THE DRAWINGS

The present invention will be further understood by reference to the following detailed description of preferred embodiments and with reference to the figures in which:

FIG. 5 shows autoradiographs of slab gels after SDS-PAGE illustrating protein samples isolated on lectin affinity columns.

DETAILED DESCRIPTION OF PREFERRED EMBODIMENTS

The 2-carbon or the propane linking the two carboxychromone groups of cromolyn was chosen as the point of conjugating cromolyn to different carriers. The choice of this site was made since it is assumed to have no role in the pharmacological activity of cromolyn. Furthermore, this is the center of symmetry of the molecule. In the original drug, a hydroxyl group is present at this position. Alkylation of this hydroxyl was not possible because the chromone heterocycle is readily opened by the strong base required for the reaction. Acylation of this hydroxyl yielded products which undergo hydrolysis in slightly alkaline solutions. Therefore, it was decided to synthesize the derivative with an amine at this position.

Figure 1A:
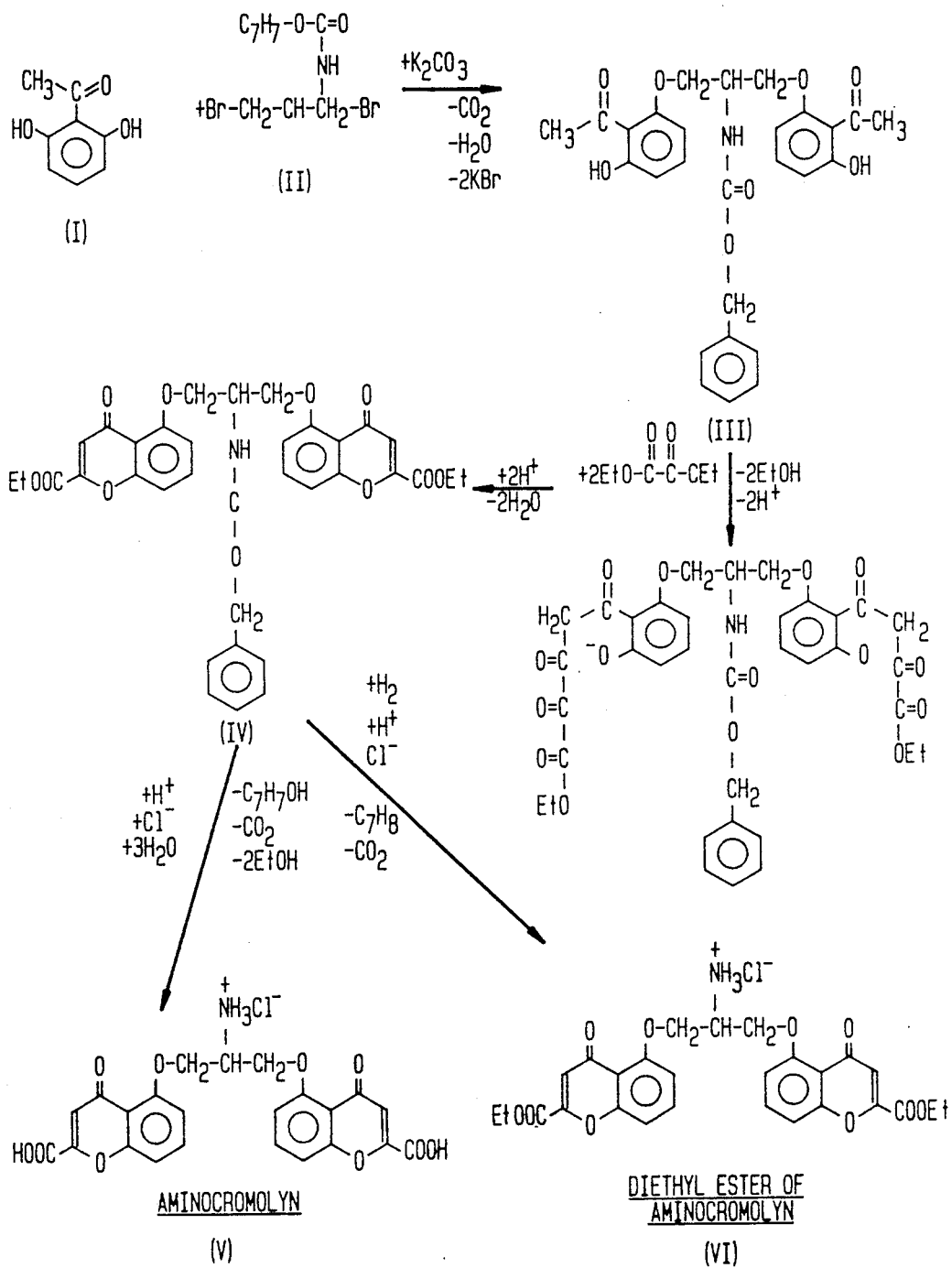
FIGS. 1A and 1B are a reaction scheme setting out the synthesis of various derivatives of cromolyn.
Figure 1B:
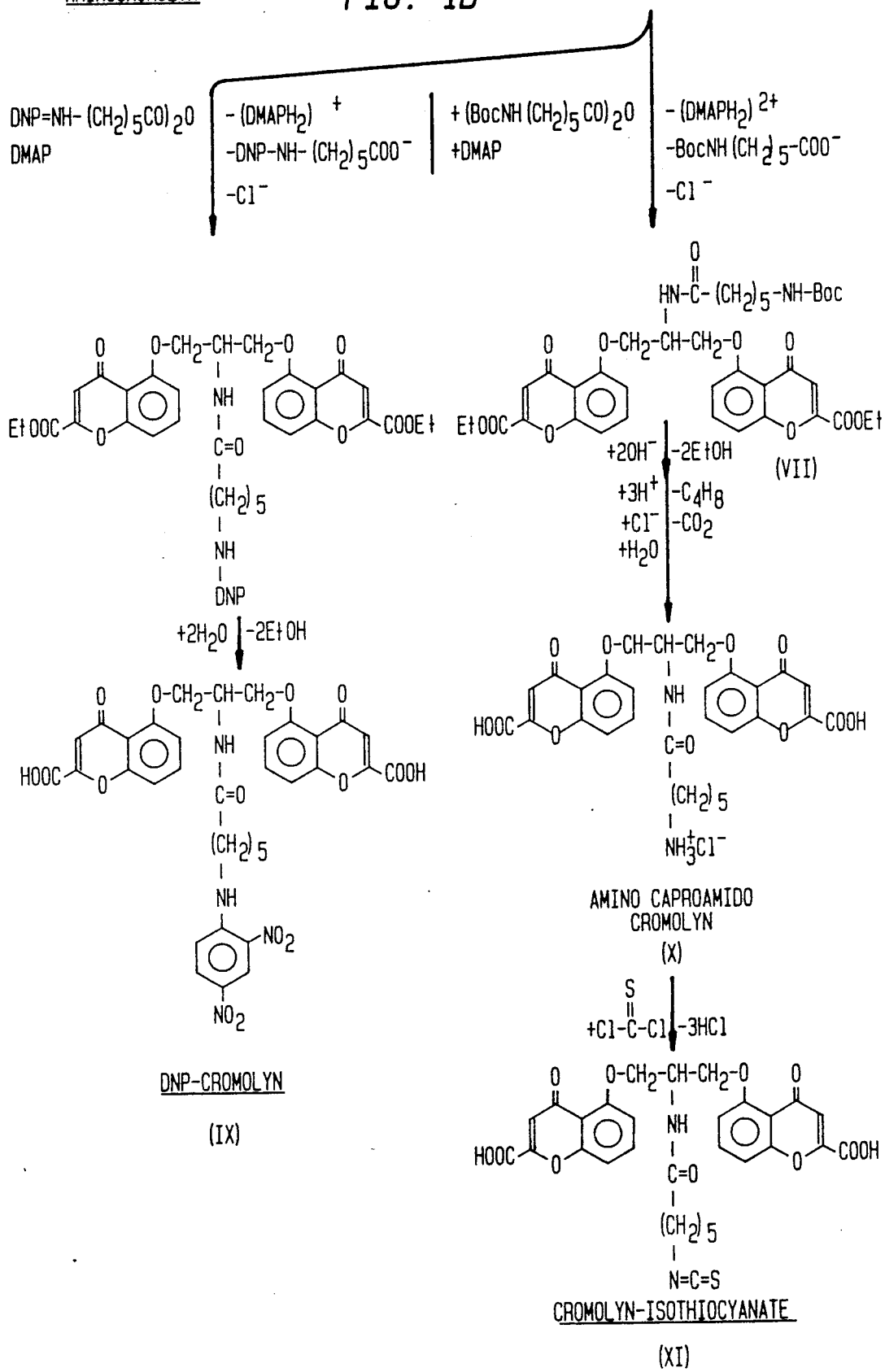

The 1,3-bis(2'-carboxychromone-5'-yloxy)-2-amidopropane (aminocromolyn) was prepared in a six step synthesis starting from 2,6-dihydroxyacetophenone, as shown in FIG. 1 and as detailed in Example 1. In FIG. 1 the abbreviations DMAP and $DMAPH_2{}^{2+}$ stand for p-N,N-dimethylaminopyridine and p-N,N-dimethylammonium-pyridinium di-cation, respectively. This cromolyn derivative with an amine group in place of the hydroxyl of the original drug, may be easily conjugated by glutaraldehyde or other cross-linking reagents to macromolecules having free amino groups, thus forming Schiff-bases with the amino group of the ligand at one end and groups such as lysyl residues on the other end.

Furthermore, once aminocromolyn is obtained, it is a relatively routine matter to derivatize the amine group as desired, in order to allow application of the cromolyn molecule in different types of conjugation procedures and in order to examine the structural requirements for its use in affinity studies. The present invention encompasses all amine derivatives. Particularly preferred derivatives for the purpose of the present invention are those in which X is $-NR^1R^2$,

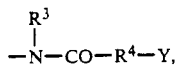

$-N=C=O$ and $-N=C-S$, wherein, $R^1$, $R^2$ and $R^3$ are hydrogen or alkyl (preferably $C_{1-5}$); $R^4$ is $C_{2-20}$ alkyl, optionally substituted, or $-CH_2)_i-C_6H_4-CH_2)_i-$, in which i is 0-10 and the phenylene group is optionally diazotized; and Y is any group which enables the attachment of the remainder of the compound to other molecules, particularly macromolecules, insoluble matrices and haptens. It may be a chemically reactive group, such as $-N=C=S$, $-N=C=O$, $-COOX^1$ ($X^1$ being halogen or any carboxyl-activating residue), $-SO_2X^2$ ($X^2$ being halogen, $-O-$alkyl or $-O-$aryl), triazinyl, epoxyl, etc. Y may also be a residue which serves as a substrate for a reactive group on the macromolecules, affinity matrices, or bifunctional agents, such as, $NR^1R^2$ ($R^1$ and $R^2$ being as defined above), $-SH$ or any electron-rich aromatic residue, such as aryl, or the like. Y may also be a hapten for which antibodies may be raised, such as dinitrophenylamino, aminonaphthalenesulfonamido, benzyl-arsonate, etc.

The synthesis of three low molecular weight derivatives of aminocromolyn is described in Examples 2-4. These derivatives were synthesized so as to allow their application in different types of conjugation procedures and in order to examine the structural requirements for their use in affinity studies. All of these derivatives have a $C_6$-spacer attached to the amine at the 2-carbon of the propane in cromolyn. This spacer carries on its other end either an amino group (aminocaproamidocromolyn—see Example 2) or an isothiocyanate (cromolyn isothiocyanate—see Example 3), or a 2,4-dinitrophenyl group (DNP-cromolyn—see Example 4). A spacer is often desirable in order to obtain the best results from the affinity chromatography as the separation of CBP is a complex combination of affinity and hydrophobic chromatography.

The synthesis of the attachable derivative, 1-(2'-carboxychromone-5-yloxy)-2-aminoethane, which is essentially the monomer of the cromolyn molecule, is described in Example 5. The material was prepared in a similar manner as aminocromolyn, by reacting 2,6-dihydroxyacetophenone with 1,2-carbobenzoxamidoethyliodide. Cyclization of the product with diethyloxalate and subsequent hydrolysis gave the product.

Compounds of a chromone structure related to cromolyn were also synthesized. 3-2'-aminoethylkhellin is a covalently attachable derivative of Khellin. Khellin is a natural product of chromone structure, shown to have smooth-muscle relaxing properties. It is the starting material for the development of all chromone-based antiallergic drugs. For syntheses of Khellin, see Gardner et al., J. Org. Chem., 15:841 (1950); Schonberg, S., J. Amer. Chem. Soc., 72:1611, 3396 (1950), incorporated by reference herein. Khellin was demethylated at position 5 by treatment with 6N HCl to yield 5-norkhellin. This intermediate was then alkylated with 2-carbobenzoxyethyl iodide. Cleavage of the carbobenzyloxy group gave the desired product. See Example 6. The amino-bis-khellin product analogous to aminocromolyn can be synthesized by the skilled artisan with readily available techniques in light of the present specification.

The primary utility for all of the cromolyn derivatives of the present invention is their use in the isolation and purification of cromolyn binding protein, which has a pronounced affinity for the drug cromolyn and to compounds of related structure. The cromolyn derivatives of the present invention allow connection of the active portion of the cromolyn molecule to macromolecules, haptens and affinity matrices which make possible highly efficient processes for purification and isolation of cromolyn binding protein. They are also useful in isolating various cytosolic components which are also useful in elucidating the mechanism of allergic response.

Cromolyn carrying matrices may be prepared by covalently attaching the cromolyn derivatives of the present invention to different carriers with controlled stoichiometry. The cromolyn derivatives are either bound directly to the affinity matrix by cross-linking with glutaraldehyde, or they are indirectly bound to the matrices by first conjugating with a macromolecule, such as bovine serum albumin (BSA), by means of cross-linking with glutaraldehyde, or other cross-linking agent, and then covalently binding the proteins to the affinity matrix. When the hapten embodiment is used, the cromolyn derivative which already bears a hapten as part of its formula may be attached to the affinity matrix or the cromolyn-protein conjugate can be derivatized with a hapten before being bound to the affinity matrix.

The affinity matrix is preferably agarose beads. However, those of ordinary skill in the art will understand that other insoluble matrices commonly used for the purpose of affinity chromatography or which in the future may be used for this purpose, may be substituted for agarose beads. The cromolyn derivative is cross-linked to an insoluble matrix having free amino groups, such as AH-Sepharose, by means of a difunctional reagent, such as glutaraldehyde, and subsequent reduction with a suitable reducing agent, such as NaBH₄. Alternatively, derivatives with a chemically-reactive group, such as aminocaproamidocromolyn, may be directly attached to an affinity matrix having activated carboxyl groups, such as CH-Sepharose 4B N-hydroxysuccinimide ester.

The cromolyn-protein conjugates may be formed in one of two ways. When X is an amine or an amine derivative which is not a reactive group, the derivative may be conjugated to the protein, such as BSA, by cross-linking the amino group with a difunctional reagent, such as glutaraldehyde, to exposed amino groups of the protein and subsequent reduction of the Schiff-bases formed with a reducing agent, such as NaBH₄. Derivatives with a reactive group, such as cromolyn isothiocyanate, may be directly reacted with the protein in alkaline buffer.

The conjugates may be further derivatized with an appropriate hapten so as to allow their use with a hapten-specific immunoadsorbent. For example, the cromolyn-macromolecule conjugates may be further derivatized with fluro-2,4-dinitrobenzene (FDNB) so as to allow their use with 2,4-dinitrophenyl (DNP) specific immunoadsorbent.

The cromolyn-macromolecule conjugates may be covalently attached to the affinity matrices in a conventional manner, such as by reaction with CNBr-activated agarose.

The cromolyn-hapten and the haptenated protein conjugates may be non-covalently immobilized on a matrix carrying a hapten-specific antibody. For example, DNP-cromolyn and the dinitrophenylated protein conjugates may be non-covalently immobilized on agarose carrying a DNP-specific IgA secreted by the murine plasma cytoma MOPC-315 (MOPC-315-Sepharose).

The various matrices of the present invention may be used to isolate the cromolyn binding protein. The protein may be isolated from the basophils or mast cells in which they naturally occur by means of the present invention. Any source of basophil cells and mast cells can be used for this purpose, although certainly immortal basophilic leukemic cell lines are preferred. The rat leukemic line RBL-2H3 (Barsumian et al (1981) *Eur. J. Immunol.*, 11, 317–323), homologous to mucosal mast cells, is one of the most convenient systems for examination of the primary processes involved in IgE-mediated secretion and a major source for identification and isolation of the cellular components involved in the above process. Thus, it is the preferred cell line for separation of cromolyn binding protein in accordance with the present invention. It should be understood, however, that the use of this cell line is by way of example only and that other similar sources of that protein can also be used in accordance with the present invention.

The cells in which there are naturally occurring cromolyn binding protein, such as RBL-2H3 cells, are lysed or their plasma membranes prepared and solublized in lysis buffer. The supernatant of the cell lysate or the solubilized membranes is then passed over a column prepared from one of the described matrices. The columns are then eluted with cromolyn in the same buffer. When appropriate matrices are used, a protein can be eluted which yields one dominant band of an apparent molecular mass of 110 kD as analyzed by autoradiography after SDS-polyacrylamide gel electrophoresis (SDS-PAGE).

Eluate containing the intact protein or its reduced form after electroelution from SDS-PAGE may be further purified by incubation on a lectin-agarose conjugate. It has been established that cromolyn binding protein is retained both on the conjugate of agarose to wheat germ agglutinin (WGA-agarose) and the conjugate of agarose to concanavalin A (ConA-agarose). The cromolyn binding protein can be completely eluted from WGA-agarose with N-acetylglucosamine. The cromolyn binding protein binds more strongly to ConA and therefore methyl-alpha-D-mannopyranoside elutes it only partially. Those of ordinary skill in the art will be able to determine other eluants which will remove the protein from the lectins using only routine experimentation. No binding was found when CBP, in either its intact or reduced form, was passed through columns packed with conjugates of agarose with the lectins soy bean agglutinin, lentil lectin or fucose binding protein.

The lectin binding is so strong that if a reducing agent, such as beta-mercaptoethanol is added to the buffer, the cromolyn binding protein can be purified on the specified lectin columns directly starting from the crude eluates from the original affinity, columns, eliminating the need for preparative SDS-PAGE and electroelution.

The affinity columns which work best in separating the cromolyn binding protein, are those columns carrying a proteincromolyn conjugate with a degree of derivatization of approximately 10 cromolyns per protein with the conjugation being by means of a cross-linking agent. Thus, a column carrying cromolyn conjugated to BSA with glutaraldehyde, with a degree of derivatization of about 10 cromolyns per BSA (BSA-(ga)-cro₁₀), is particularly useful in yielding one dominant band of an apparent molecular mass of 110 kD as analyzed after SDS-PAGE. Any protein with a molecular mass greater than 30,000, which is not precipitated by dialdehydes, may be substituted for BSA and can be expected to be particularly useful when bound to an appropriate carrier in separation of a cromolyn binding protein. Ovalbumin is one example of such an operable protein. Furthermore, while it is important that the protein be bound by a cross-linking agent to the matrix, other cross-linking agents beside glutaraldehyde may be used, although glutaraldehyde is preferred.

With all columns which had cromolyn bound directly to the matrix and columns in which the ligand was conjugated with an artificial poly-amino acid, no membranal protein could be eluted. This implies that the chromatography is not a classical affinity type, but a complex affinity and less specific hydrophobic interaction. Nevertheless, all of the affinity matrices bearing the cromolyn derivatives of the present invention have utility as they may be effective in isolating one more cytosolic components, which are also useful in elucidating the mechanism of allergic response.

The cromolyn binding protein (also known as channel-forming protein) separated from the RBL cells by the BSA-(ga)-cro₁₀-agarose column following electroelution from SDS-PAGE and purification on a WGA-agarose column, shows an apparent molecular mass of 110,000 in intact form and 50,000 in reduced form. Its apparent abundance on RBL-cells is approximately 10,000 copies per cell. Both the intact and reduced form are glycosylated. The preliminary yield of isolation is approximately 0.5 μg from 100 ml cells. The amino acid composition of the reduced form is as set forth in Table I hereinabove.

The protein CBP can be used for controlling calcium flux and histamine release. The addition of such protein or its introduction into cells or cell membranes enhances calcium passage through such membranes. CBP is also useful in developing assays for blockers of $Ca^{2+}$ channels of this kind. Specific antibodies raised against this protein have utility in inhibiting the immunologically-mediated histamine release. Antibodies raised against cromolyn binding protein inhibit more than 90% of immunologically-mediated histamine release from the RBL-2H3 cells (as tested by the fluorimetric method according to Shore (*J. Pharmacol. Exp. Ther.*, 127, 182 (1959)) and by $^3$H-Serotonin secretion. The cromolyn binding protein is useful in permitting such antibodies to be obtained and such antibodies themselves have pharmacological activity.

The processes of preparing the cromolyn derivatives of the present invention, the preparation of immobilized cromolyn derivatives on matrices, and isolation of the cromolyn binding protein in accordance with the present invention are further illustrated by the following examples:

EXAMPLE 1

Aminocromolyn (V)

2,6-dihydroxyacetophenone (I)

2,6-dihydroxyacetophenone is synthesized from resorcinol as described by Russell et al, Organic Synthesis Coll., Vol. 3, pp. 281–285.

b,b'-dibromo-isopropylammonium bromide 7 g (76.9 mmol) serinol were dissolved in 60 ml conc. HBr (48%). This solution was saturated with gaseous HBr at 0° C. and transferred into a reactor made from stainless steel and coated inside with Teflon. The reactor was tightly closed and heated in a stirred oil bath for 3 h at 180° C. Thereafter, the content was diluted with water to 500 ml, decolorized with charcoal and evaporated to dryness. The residue was taken up in 500 ml ethanol, and again evaporated. This step was repeated once more. Now the evaporation was interrupted as crystals started to appear. After addition of 100 ml EtOAc and incubation at −20° C. the product was filtered off, washed twice with cold EtOAc and dried in vacuo, yielding 21.2 g (92.5%) b,b'-isopropylammonium bromide. Thin layer chromatography (TLC) showed a single ninhydrin stained spot with a $R_F$ value of 0.69 in EtOH/AcOH/$H_2O$ (8/1/1, v/v).

1,3-dibromo-2-carbobenzoxamidopropane (II)

To an ice cold solution of 12 g (40.3 mmol) b,b'-dibromo-isopropylammonium bromide in 50 ml $H_2O$ were added 9.2 g (60 mmol) benzylchloroformate. Thereafter 50 ml of 5 M sodium hydroxide were added dropwise, whereupon a colorless oily precipitate appeared. The mix was allowed to stand in the ice for 10 min more, and then the precipitate was collected on a sinter, washed with cold water and dried in vacuo over $P_2O_5$. The dry crude product was recrystallized from petrolether (80°–100° C.), yielding 7.6 g (54%) 1,3-dibromo-2-carbobenzoxamidopropane. The product was characterized by NMR analysis. $^1$H NMR (CDCl$_3$): d 7.4 (s, 5H, aromatic), 5.14 (s, 2H, —CH$_2$), 4.2 (m, 1H, —CH), 3.6 (m, 4H, —CH$_2$).

1,3-bis(6'-hydroxy-acetophenon-2'-yloxy)-2-carbobenzoxamidopropane (III)

15.2 g (0.1 mol) 2,6-dihydroxyacetophenone, 17.5 g (0.5 mol) II and 7 g (0.505 mol) anhydrous K$_2$CO$_3$ were filtered off and the filtrate was evaporated to dryness. The residue was taken up in 150 ml CHCl$_3$. A yellow precipitate formed, which turned out to be mainly unreacted 2,6-dihydroxyacetophenone. It was filtered off, and the filtrate was evaporated to dryness. To the residue were added 50 ml ether and 50 ml $H_2O$, and the mixture was stirred at room temperature (RT) for 2 h. The colorless crystalline material, which did not dissolve either in ether or in water, was filtered off, washed several times with water and ether and dried in vacuo over P$_2$O$_5$, yielding 2.27 g (9.2%) 1,3-bis(6'hydroxyacetophenon-2'-yloxy)-2-carbobenzoxamidopropane. TLC showed a single spot with a $R_F$ value of 0.28 in PE/EtOAc (3/1, v/v). The product was further characterized by NMR analysis. $^1$H NMR (CDCl$_3$): d 7.4 (s, 7H, —C$_6$H$_5$ & p-aromatic), 6.5 (q, 4H, m-aromatic), 5.14 (s, 2H, —CH$_2$ of benzyl), 4.6 (m, 1H, —CH of propane-2), 4.3 (d, 4H, —CH$_2$ of propane-1,3), 2.62 (s, 6H, —CH$_3$).

1,3-bis(2'-carboxychromone-5'-yloxy)-2-carbobenzoxamido-oropane diethyl ester (IV)

464 mg (20.2 mmol) sodium were dissolved in 5.8 ml boiling ethanol. After the metal had dissolved completely, the solution was allowed to cool down, before 11.6 ml dry ether were added to the solution. To this was added a suspension of 2.29 g (4.65 mmol) III in 2.9 ml freshly distilled diethyloxalate, 5.8 ml abs ethanol and 5.8 ml benzene. This mixture was refluxed gently for 24 h. Then it was taken up in 100 ml ether, whereupon the sodium salt of the oxoester precipitated. This was collected on a glass filter, washed twice with ether and taken up in water. The little non-dissolving material was filtered off, and from the filtrate the oxoester was precipitated with 2N HCl. It was collected on a glass filter, washed and dried. The dry material was dissolved in a mix of 500 ml ether, 50 ml ethanol and 5 ml conc. HCl. This solution was stirred at RT overnight, then it was evaporated to dryness. The residue was taken up in 200 ml EtOAc and 200 ml $H_2O$. The aqueous phase was separated and discarded, while the organic phase was washed twice with 0.2 M NaHCO$_3$, twice with $H_2O$ and once with sat. NaCl. It was dried over MgSO$_4$ and evaporated to dryness. The residue was recrystallized from little EtOH, yielding 1962 mg (64%) 1,3-bis(2'-carboxychromone-5'-yloxy)-2-carbobenzoxamido-propane diethyl ester. TLC showed a single spot with a $R_F$ value of 0.6 in petrolether/EtOAc (1/1, v/v).

1,3-bis(2'-carboxychromone-5'-yloxy)-2-aminopropane hydrochloride (aminocromolyn) (V)

Figure 2A:
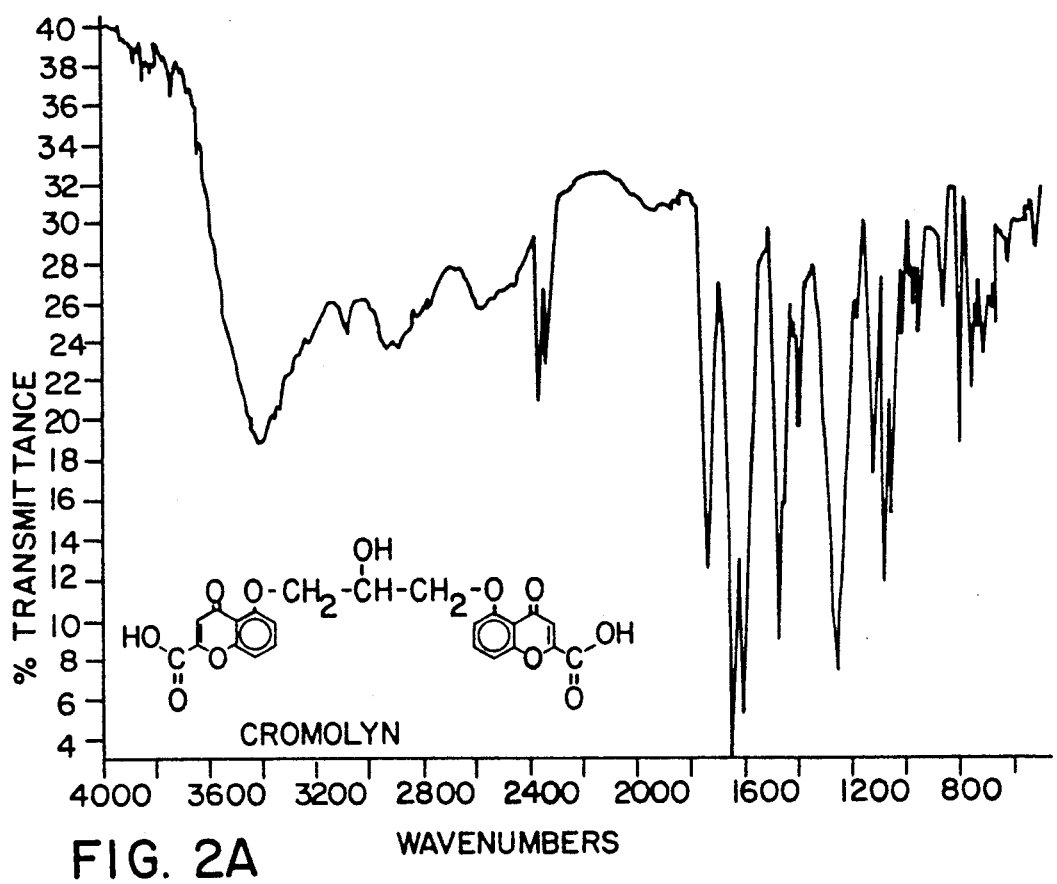
FIG. 2A-2D illustrate the IR spectra of cromolyn, aminocromoly, aminocaproamidocromoly, and cromolyn-isothiocyanate, respectively (1.5% KBr-pellet)
Figure 2B:
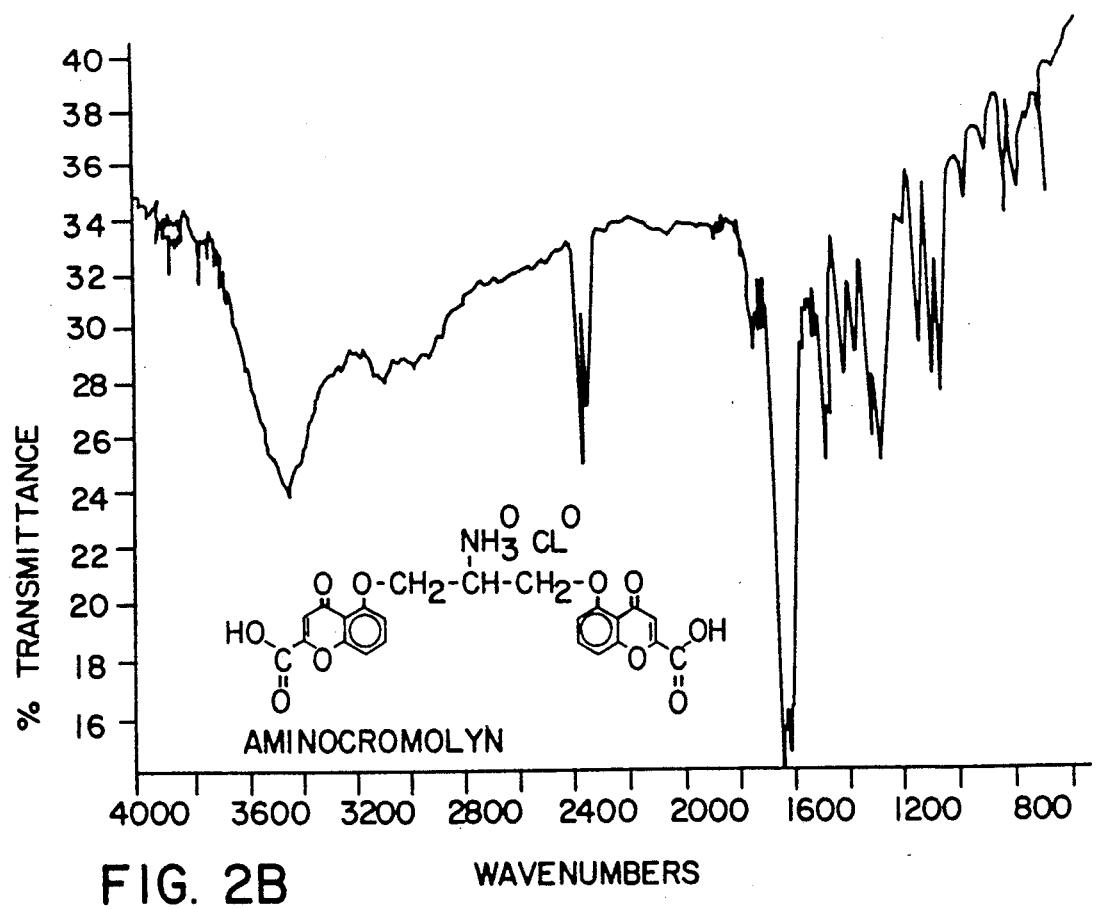

1000 mg (1.52 mmol) of IV were refluxed for 3 h in 15 ml of AcOH/conc. HCl (3/1, v/v). A colorless precipitate appeared. The mixture was allowed to cool in ice, and the precipitate was filtered off, washed with little AcOH/conc. HCl (3/1, v/v), water, EtOH and ether and resuspended in 300 ml $H_2O$. This suspension was titrated with 2N NaOH to pH 9, until a clear solution was obtained. This brownish solution was decolorized with charcoal and thereafter acidified with 2N HCl, upon which the hydrochloride of aminocromolyn appeared as a colorless voluminous precipitate. The precipitate was collected, washed with $H_2O$, EtOH and ether and dried in vacuo over $P_2O_5$, yielding 525 mg (68.6%) aminocromolyn. TLC showed a single spot with a $R_F$ value of 0.5 in dimethylformamide/EtOH/AcOH (5/5/1, v/v), which stained with ninhydrin. The product was further characterized by UV and IR absorption spectrophotometry. The IR spectra is shown in FIG. 2B. The UV absorption spectrum of the product was over the range of 400 nm —200 nm quantitatively identical to that of the purified commercial cromolyn. $e_{324\ nm}$ 8500 $M^{-1}cm^{-1}$, $e_{236\ nm}$ 29200 $M^{-1}cm^{-1}$; solvent 0.1 N aq. $NaHCO_3$.

EXAMPLE 2

Aminocaproamidocromolyn (X)

1,3-bis(2'-carboxychromone-5'-yloxy)-2-aminopropane diethylester hydrochloride (aminocromolyn diethyl ester) (VI)

1.5 g (2.28 mmol) IV was dissolved in 20 ml dioxane. 80 ml EtOH, 3 ml 2N HCl and 100 mg 10% Pd on charcoal were added, and the suspension was hydrogenated at RT and atmospheric pressure for 3 h. Then the catalyst was filtered off and washed with 20 ml dioxane and 100 ml EtOH. The combined filtrates were evaporated to a residual volume of 30 ml. Upon incubation at −20° C. the hydrochloride of aminocromolyn diethylester crystallized. Yield: 913 mg (71.6%). TLC showed a single spot with a $R_F$ value of 0.52 in nBuOH/AcOH/$H_2O$ (8/1/1, v/v).

1,3-bis(2'-carboxychromone-5'-yloxy)-2-(6"-N-tBoc-amidocaproamido)-propane diethylester (VII)

1300 mg (2.32 mmol) VI and 872 mg (7.15 mmol) p-N,N-dimethylaminopyridine were dissolved in 80 ml dry $Me_2SO$ (solution 1). 2146 mg (9.3 mmol) 6"-N-tBoc-amidocaproic acid were dissolved in 25 ml dry dioxane (solution 2). 1121 mg (4.65 mmol) dicyclohexylcarbodiimide were added to solution 2, and it was stirred at RT. Dicyclohexylurea precipitated from the solution, and after 30 min the mix was filtered straight into solution 1. The combined solutions were stirred overnight at RT, and then it was taken up in 500 ml EtOAc and 500 ml $H_2O$. The aqueous extract was discarded, and the organic phase was extracted twice more with water, three times with 0.2 M $NaHCO_3$, three times with 1% AcOH, twice more with $H_2O$ and finally once with sat. NaCl. Then it was dried over $MgSO_4$ and evaporated, until crystals started to appear. Thereafter the solution was left to crystallize at −20° C., yielding 1410 mg (82.5%) 1,3-bis(2'-carboxychromone-5'-yloxy)-2-6(6"-N-tBoc-amidocaproamido)-proamido)-propane diethylester. TLC showed a single spot with a $R_F$ value of 0.29 in EtOAc/petrolether (9/1, v/v).

1,3-bis (2'-carboxychromone-5'-yloxy)-2-(6"-N-tBoc-amidocaproamido)-propane (VIII)

1000 mg (1.36 mmol) of VII were dissolved in 50 ml dioxane/EtOH (1:1, v/v). To the stirring solution were added dropwise 1.36 ml 2 N NaOH. The disodium salt precipitated almost immediately, and after 10 min it was filtered off, washed with dioxane and ether and dried. The dry material was dissolved in 25 ml $H_2O$ and the diacid was precipitated with 2N HCl. Yield: 725 mg (78%) 1,3-bis(2'-carboxychromone-5'-yloxy)-2-(6"-N-tBoc-amidocaproamido)-propane. TLC showed a single spot with a $R_F$ value of 0.67 in EtOH/AcOH/$H_2O$ (8/1/1/, v/v).

1,3-bis(2'-carboxychromone-5'-yloxy)-2-(6"-aminocaproamido)propane hydrochloride (aminocaproamidocromolyn) (X)

Figure 2C:
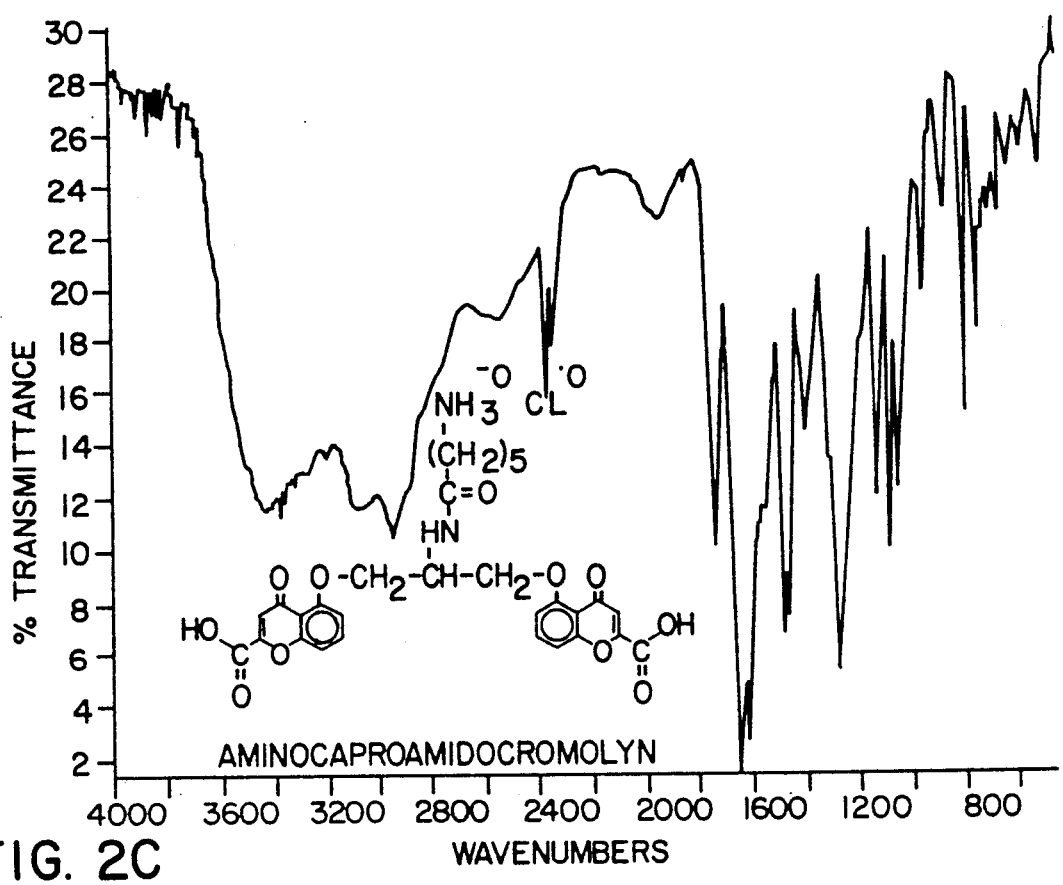

623 mg (0.916 mmol) of VIII were dissolved in 25 ml dioxane. To the stirring solution were added 5 ml HCl in dioxane (4.7M). The solution became turbid, and a yellow greasy precipitate appeared. The mixture was stirred at RT for 2 h, and then the ppt., which was sticking to the flask, was decanted and taken up in little ethanol. Thereupon it formed crystals. After addition of 20 ml ether the flask was left at −20° C. for complete crystallization. The crystals were collected on a sinter and washed with cold EtOH, ether and low boiling petrolether. Yield: 501 mg (89%) aminocaproamidocromolyn. TLC showed a single spot with an $R_F$ value of 0.27 in EtOH/AcOH/$H_2O$ (8/1/1, v/v), which stained with ninhydrin. The product was further characterized by UV and IR absorption spectrophotometry. The IR spectrum is shown in FIG. 2C. The UV absorption spectrum of the product was over the range of 400 nm-200 nm quantitatively identical to the spectrum of purified commercial cromolyn.

EXAMPLE 3

1,3-bis-(2'-carboxychromone-5'-yloxy)-2-(6"-isothiocyanate-caproamido)-propane (cromolyn-isothiocynate) (XI)

Figure 2D:
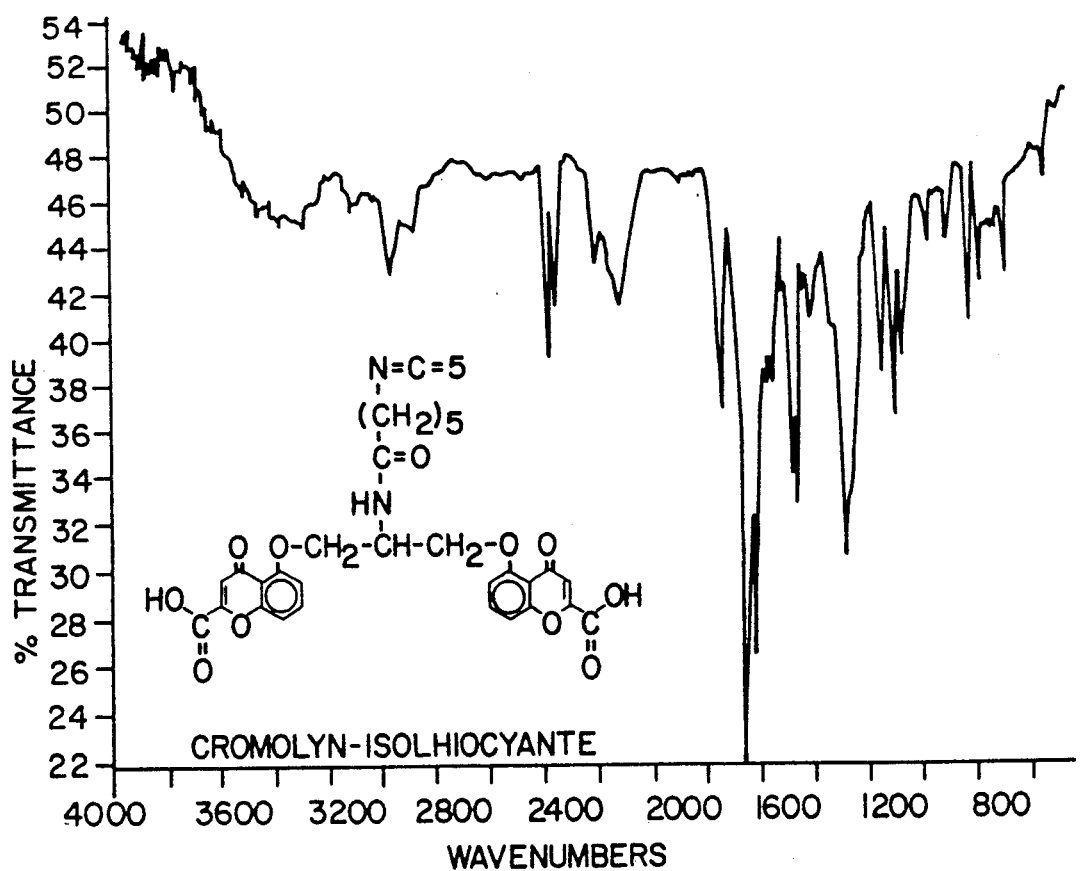

0.1 ml vacuum distilled thiophosgene were suspended in 3 ml $H_2O$ at RT. To the stirring suspension was added a solution of 100 mg (0.162 mmol) aminocaproamidocromolyn and 300 mg $NaHCO_3$ in 3 ml $H_2O$. The mix was stirred at RT for 4 h, then the product was precipitated with 2N HCl. The ppt was collected on a sinter, washed several times with water and dried in vacuo over $P_2O_5$, yielding 77 mg (76%) cromolyn-isothiocyanate. TLC showed a single spot with a $R_F$ value of 0.59 in EtOH/AcOH/$H_2O$ (8/1/1/, v/v). The product was further characterized by UV and IR spectrophotometry. The IR-spectrum is shown in FIG. 2D. The UV-spectrum of the product was over the range from 400-230 nm quantitatively identical to that of aminocromolyn or commercial cromolyn. The IR-spectrum displayed the peak characteristic for —NCS.

EXAMPLE 4

1,3-bis(2'-carboxychromone-5'-yloxy)-2-(6"-N-(2''',4'''-dinitrophenyl)-amidocaproamido)-propane (DNP-cromolyn) (IX)

This material was synthesized from aminocromolyn diethyl ester (VI) and N-2,4-DNP-e-aminocaproic acid essentially as described for the synthesis of VIII from aminocromolyn diethyl ester and N-tBoc-e-amidocaproic acid via VII. From 207 mg (0.37 mmol) of VII, 115 mg (42%) DNP-cromolyn were obtained. TLC showed a single yellow spot with an $R_F$ value of 0.6 in EtOH/AcOH/$H_2O$ (8/1/1, v/v).

EXAMPLE 5

1-(2'-Carboxychromone-5-yloxy)-2-aminoethane

This substance is an attachable derivative of 1-(2'-carboxychromone-5-yloxy)-2-hydroxyethane, which is essentially the monomer of the cromolyn molecule. The material was prepared in a similar manner as aminocromolyn, namely by reacting 2,6-dihydroxyacetophenone with 1,2-carbobenzoxamidoethyl iodide, cyclization of the product with diethyloxalate and subsequent hydrolysis.

EXAMPLE 6

5-(2'-Aminoethyl)khellin

This substance is an attachable derivative of Khellin. Khellin was demethylated at position 5 by treatment with 6N HCl to yield 5-norkhellin, which was alkylated with 2-carbobenzoxyethyl iodide. Cleavage of the protecting group gave the desired product.

EXAMPLE 7

Conjugation of Aminocromolyn to BSA with glutaraldehyde

A solution of BSA in 0.1 M NaHCO$_3$ (10 mg/ml) was adjusted to pH 9.5 with aq. NaOH. To the stirring sample aminocromolyn (hydrochloride) together with two equivalents NaHCO$_3$ were added. For a control compound one equivalent of NH$_4$Cl was added instead. Then glutaraldehyde as 5%-solution in 80 mM NaHCO$_3$ was added dropwise. The solution, which developed a deep yellow color, was stirred for 5 h at RT, then it was cooled in ice and treated with 70 mM NaBH$_4$. The sample was stirred on ice for more 4 h., upon which the yellow color disappeared. Then it was dialyzed extensively against repeated changes of phosphate buffered saline (PBS). The protein concentration (BSA) in the dialysate was determined as the amount of protein weighed in over the volume of the dialysate. The degree of derivatization, namely n=(cromolyn/(-BSA), was determined by light absorption of the dialysates at 325 nm ($e_{325nm}$(cromolyn)=8500 mol$^{-1}$cm$^{-1}$). The dialysates were used as such for all purposes and were lyophilized for long term storage. The different reaction mixtures and resulting conjugates (BSA-(ga)-cro$_n$) are summarized in Table II.

TABLE II

| [AC]:[BSA]:[CH2(CH2CHO)2] in reaction mixture | Degree of derivatization |
|---|---|
| 13:1:167 | 3.8 |
| 26:1:167 | 9.7 |
| 33:1:167 | 12.5 |
| 40:1:167 | 15.9 |
| 53:1:167 | 17.5 |
| 130:1:167 | 21 |
| 40:1:33 | 5 |

[AC], [BSA] and [CH$_2$(CH$_2$CHO)$_2$] are the respective molar concentrations of aminocromolyn, BSA, and glutaraldehyde. Degrees of derivitization are expressed as number of cromolyn moieties bound per mole BSA.

EXAMPLE 8

Conjugates of cromolyn isothiocyanate with BSA

A solution of BSA in 0.1 M NaHCO$_3$(10 mg/ml) was adjusted to pH 10.5 with aq. NaOH. To the stirring sample was added cromolyn isothiocyanate and two equivalents NaHCO$_3$. The solution was stirred for 4 h at RT. Then it was dialyzed extensively against repeated changes of PBS. The degrees of derivation of the conjugates were determined as described above. The different reaction mixtures and resulting conjugates (BSA-(itc)-cro$_n$) are summarized in Table III.

TABLE III

| [CITC]:[BSA] in reaction mixture | Degree of Derivitization |
|---|---|
| 4.3 | 4.3 |
| 10.6 | 6.5 |
| 21.3 | 8.8 |
| 42.6 | 13.5 |
| 107 | 25 |

[CITC] and [BSA] are the respective molar concentrations of cromolyn-isothiocyanate and BSA. Degrees of derivatization are expressed as number of cromolyn moieties bound per mole BSA.

EXAMPLE 9

Conjugation of cromolyn-isothiocyanate to polyalanine-lysine

Cromolyn-isothiocyanate was reacted with the synthetic amino acid polymer poly-alanine-lysine (A—L) ([A—L]=3.75 mg/ml =0.084 M peptide bond) under the same conditions employed for the reaction with BSA. The different reaction mixtures and resulting conjugates (A—L-(itc)-cro$_{m/pb}$, in which m/pb is the number of cromolyn moieties bound per peptide bond of A—L) are summarized in Table IV.

TABLE IV

| [CITC]:[—CONH—] in reaction mixture | Degree of Derivitization |
|---|---|
| 0.02 | 0.02 |
| 0.038 | 0.036 |
| 0.076 | 0.066 |
| 0.19 | 0.104 |

[CITC] AND [—CONH—] are the respective molar concentrations of cromolyn-isothiocyanate and of peptide bonds in (Ala$_{22}$Lys)$_n$. Degrees of derivatization are expressed per mole peptide bond of (Ala$_{22}$Lys)$_n$

EXAMPLE 10

Derivatization of the conjugates with FDNB

The dialysates containing BSA-cromolyn conjugate in PBS were brought to pH 8.5 by addition of aq. Na$_2$CO$_3$. These solutions were treated with 16 mM of 1-fluoro-2,4-dinitrobenzene (FDNB). The sample was stirred for 3 h at RT, then it was dialysed extensively against repeated changes of PBS. The degree of derivatization was determined by the differential absorption of the of the dialysates at 400 nm ($e_{400nm}$(DNP)=7200 M$^{-1}$cm$^{-1}$) and 354 nm ($e_{354nm}$(DNP)=17400 M$^{-1}$cm$^{-1}$, $e_{354nm}$(cromolyn)=3390 M$^{-1}$cm$^{-1}$, A$_{354 mn}$=[DNP]×17400 M$^{-1}$+[cromolyn]×3390 M$^{-1}$).

EXAMPLE 11

Cromolyn-Sepharose 1 g freeze dried AH-Sepharose 4B was suspended in 10 ml of 0.5 M aq. NaCl and left to swell for 3 h. Then it was washed with 0.5 M aq. NaCl and equilibrated in 0.1 M NaHCO$_3$. 100 mg aminocromolyn (hydrochloride) and 35 mg NaHCO$_3$ were dissolved in 10 ml 0.1 M aq. NaHCO$_3$. The gel was added to this solution, and to the stirring suspension were added dropwise 0.5 ml 5% glutaraldehyde in 80 mM aq. NaHCO$_3$. The suspension was shaken overnight at RT before it was cooled in ice and treated with 0.5 ml 10% aq. NaBH$_4$. The sample was shaken at 4° C. for 3 h, and then the beads were collected on a glass filter, washed thoroughly with 0.1 M NaHCO$_3$, followed by 0.1 M borate, 1 M NaCl pH 8.5 and finally 0.2 M borate, 0.16 M NaCl, 2 mM CaCl$_2$ pH 7.4 (BBS-Ca$^{2+}$). The matrix was stored in BBS-Ca$^{2+}$ 0.1% NaN$_3$. Unbound aminocromolyn was detected in the filtrate by its absorption at 325 nm. From the difference between total and unbound, the amount of bound aminocromolyn was found to be 35 mg (35%).

EXAMPLE 12

Cromolyn-Sepharose 1 g freeze dried activated CH-Sepharose 4B was suspended in 25 ml of 1 mM HCl for 5 min. Then, the swollen gel was washed with 1 l of 1 mM HCl. 100 mg aminocaproamidocromolyn and 27 mg NaHCO$_3$ were dissolved in 4 ml 0.1 M NaHCO$_3$, 0.5 M NaCl pH 8.5 (coupling buffer). Now the washed gel was added to this solution, and this suspension was shaken overnight at 4° C. Then the beads were collected on a glass filter, washed three times with 0.1 M phosphate, 0.5 M NaCl pH 8.0 (Buffer N), three times alternating with 0.1 M acetate, 1 M NaCl pH 4.0 (Buffer A) and 0.1 M borate, 1 M NaCl pH 8.5 (Buffer B) and finally with BBS-Ca$^{2+}$. The matrix was stored in BBS-Ca$^{2+}$ 0.1% NaN$_3$. The amount of bound aminocaproamidocromolyn was found to be 22 mg (22%).

EXAMPLE 13

Derivatization of agarose with the various conjugates

The cromolyn-macromolecule conjugates were covalently attached to CNBr-activated Sepharose 4B essentially as described in Cuatrecasas, P. (1987), *J. Biol. Chem.*, 245, 3095. Typically, 3 ml dialysate containing approximately 30 mg of conjugate in PBS were brought to pH 8.5 and added to 4 ml activated gel. Usually degrees of derivatization of approximately 5 mg conjugate per ml gel were achieved.

EXAMPLE 14

DNP-specific immunoadsorbent (MOPC-315-Sepharose)

Affinity purified DNP-specific IgA secreted by the murine plasma cytoma MOPC-315 was immobilized on Sepharose 4B by the CNBr-method (Cuatrecasas, supra). Unbound protein in the filtrate was determined by its absorption at 280 nm (1 mg/ml protein=1.4 O.D.), and from the difference to the total amount of protein the degree of derivatization was found to be 4.4 mg MOPC-315 per ml gel.

EXAMPLE 15

Isolation of cromolyn binding protein from RBL cell lysates using affinity chromatography Surface radioiodination of RBL cells 2.5×10$^8$ RBL-2H3 cells were harvested from tissue culture and washed three times in PBS. To the cell pellet were added 90 ul lactoperoxidase (0.5 mg/ml) in PBS, 10 ul 0.15 mM KI, 40 ul Na$^{125}$I solution (100 mCi/ml) and 20 ul 0.03% H$_2$O$_2$. After 4, 8, 12 and 16 min further 90 ul of the lactoperoxidase solution and 20 ul 0.03% H$_2$O$_2$ were added, and after 20 min the reaction was terminated by addition of 50 ml PBS. The cells were sedimented and washed another three times with PBS.

Preparation of the cell lysate

The radiolabelled washed cells were lysed in 0.2 M borate, 0.16 M NaCl, 2 mM CaCl$_2$, pH 7.4 (BBS-Ca$^{2+}$) supplemented with 0.5% Triton X-100, leupeptin (0.75 ug/ml), pepstatin (2.25 ug/ml), and aprotinin (0.6 TIU/ml). 2 ml of this lysis buffer were employed per 10$^8$ cells. The crude lysate was centrifuged 1 h at 18,000 rpm. The supernatant was processed immediately further, while the pellet was discarded.

Preparation of solubilized purified RBL-plasma membranes

RBL plasma membranes were isolated from surface labelled cells on a discontinuous sucrose density gradient as described elsewhere (Sagi-Eisenberg R. et al, (1984) *Imm. Lett.*, 8, 43–47). The purified membranes were washed once with BBS-Ca$^{2+}$ and solubilized in the lysis buffer described above. 2 ml lysis buffer were employed per quantity of membranes equivalent to 10$^8$ cells. The the unsolubilized components were sedimented at 18,000 rpm, and the supernatant was processed immediately further.

Affinity chromatography

A "Polyprep" column (Bio-Rad) was packed with 0.5 ml of the matrix-gel and washed with BBS-Ca$^{2+}$ 1% Triton X-100. Cell lysate or solubilized membranes obtained from 2.5×10$^8$ cells (5 ml) were passed over this column during 3 h. The column was washed overnight with BBS-Ca$^{2+}$ containing 0.5% Triton X-100 and 0.15% soybean lipids (buffer I) at 4° C. at a delivery speed of 25 ml/h. Then the column was first eluted with 20 mM commercial cromolyn in buffer I at 4° C. at a elution rate of 0.25 ml/h. Ten fractions of 0.5 ml each (first fraction only 0.33 ml) were collected. Thereafter the column was eluted further with 20 mM cromolyn and 10 mM DTT in buffer I at the same slow rate. Again 10 fractions (No. 1 0.33 ml, No. 2 to 10 each 0.5 ml) were collected.

EXAMPLE 16

Isolation of CBP using immunoadsorption 0.5 ml MOPC-315-Sepharose were washed with BBS-Ca$^{2+}$ on a glass filter. The washed gel was incubated with 5 ml of a 1:10 dilution of DNP-BSA-cromolyn (dialysate containing 10 mg/ml conjugate in PBS) in BBS-Ca$^{2+}$ at 4° C. for 15 min. Then the gel was washed thoroughly, first with BBS-Ca$^{2+}$ then with BBS-Ca$^{2+}$ 1% Triton X-100 and packed in a polyprep column. Cell lysate or solubilized membranes prepared in the same manner as in Example 15 were passed over this column, then the column was washed for 40 h with BBS-Ca$^{2+}$ containing 0.5% Triton X-100 and 0.15% soybean lipids (buffer I) at 4° C. at a delivery speed of 15 ml/h. Then, the column was first eluted with 5 mM Ne-DNP-lysine in buffer I at 4° C. at a elution speed of 1 ml/h. 10 fractions of 0.5 ml each (first fraction only 0.33 ml) were collected. Thereafter the column was eluted further with alkaline buffer I of pH 10.5. Again 10 fractions (No. 1 0.333 ml, No. 2 to 10 0.5 ml each) were collected. Thereafter the column was washed with 0.1 M NaHCO$_3$ pH 10.5, acetate buffer (pH 4) and borate buffer (pH 9) alternatingly and finally with BBS-Ca$^{2+}$. After this treatment the column was found to be free from conjugate and other proteins and could re reused.

EXAMPLE 17

Analysis of the eluate fractions by SDS-polyacrylamide gel electrophoresis (SDS-PAGE)

SDS gel electrophoresis was done with the discontinuous buffer system described by Laemmli, U. K. (1970), *Nature*, 227, 680. Nonreduced samples were run in a 7-10% polyacrylamide gradient gel with the following molecular weight standards: thyroglobulin (669 kD), ferritin (440 kD), catalase (232 kD), lactate dehydrogenase (140 kD) and BSA (67 kD). Reduced samples were run in a 10-15% gradient gel with the following standards: phosphorylase, B (94 kD), BSA (67 kD), ovalbumin (43kD), carbonic anhydrase (30 kD), soybean trypsin inhibitor (20.1 kD) and a-lactalbumin (14.4 kD). The gels were fixed in MeOH/AcOH/H$_2$O (50/12/38, v/v) and silver-stained as described by Goldmann, D. et al (1981), *Science*, 211, 1437. They were dried in a vacuum gel drier and exposed on prewashed Kodak XAR-5 film at $-70°$ C.

1.5 ml of an eluate containing the 110 kD protein were treated with 0.75 ml of 3-fold concentrated nonreducing sample buffer at RT and subjected to SDS-PAGE (7-10% polyacrylamide gradient). Then both the left and right margin of the slab gel, which contained the traces of the molecular weight markers, were removed and stained with Coomassie brilliant blue. From the core of the gel the upper and lower margins were removed at positions 20 mm upward and 20 mm downward resp. of the estimated position of the 110 kD protein. The remaining gel piece was sliced horizontally into 20 slices of 2 mm thickness each. To each of these slices 30 ul of 50% (w/v) glycerol, M Tris-base, 0.1% SDS, 2 mg/ml bromophenol blue, and they were soaked in this buffer overnight at 4° C. Then their radioactivity was measured, and the two slices containing the activity peak were pooled and placed into an electroelution cell. This was filled with the usual electrophoresis buffer and subjected to a potential of 100 V for 30 min and 50 V for further 30 min. Then the blue layer having accumulated above the positive membrane was aspirated. The protein so obtained is cromolyn binding protein in substantially pure form.

EXAMPLE 18

SDS-PAGE results of various methods of separation

Protein samples isolated by various affinity procedures of the present invention, and a control, were subjected to SDS-PAGE. Autoradiographs of slab gels after SDS-PAGE are shown in FIG. 3.

Figure 3:
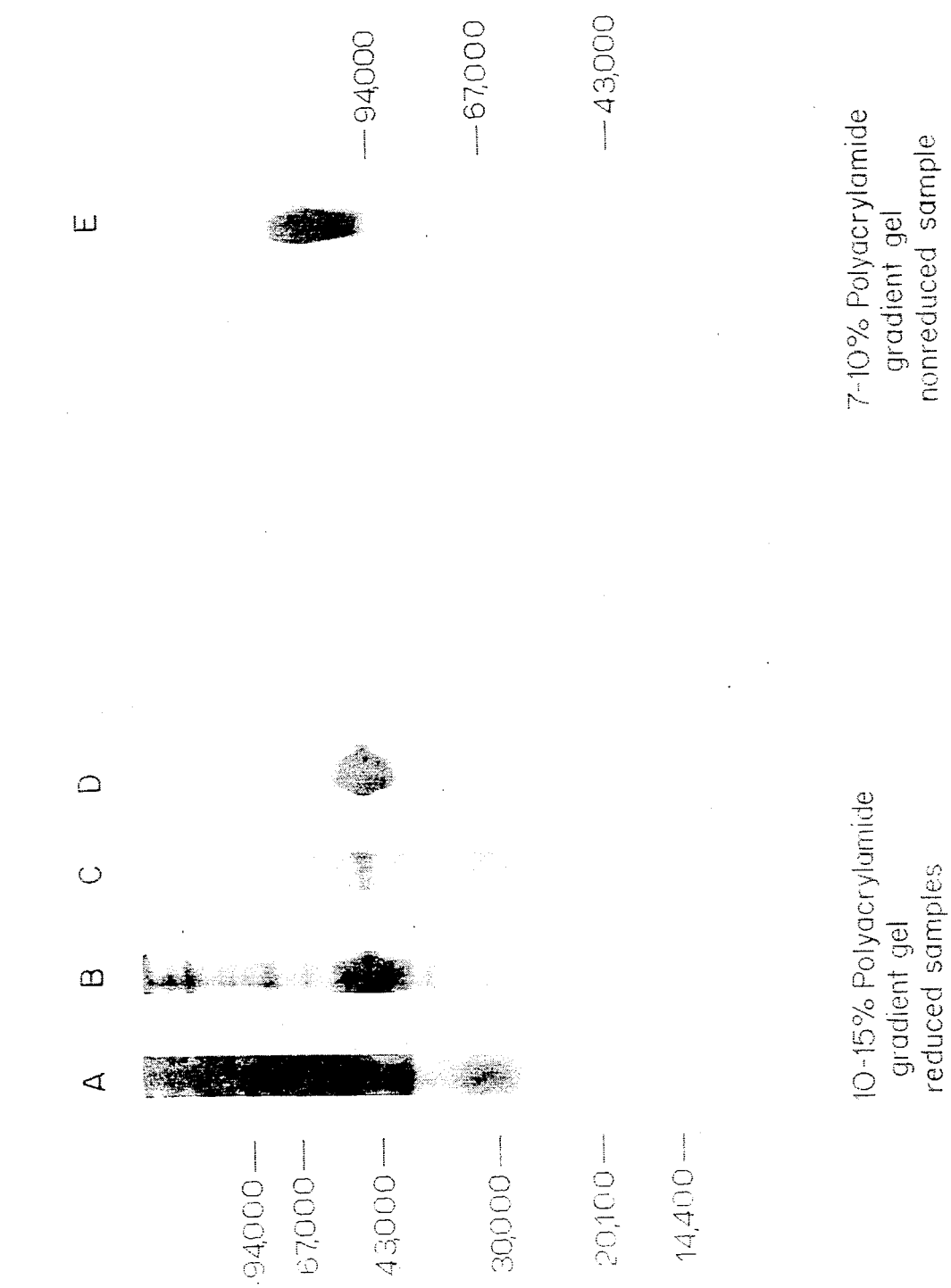
FIG. 3 shows autoradiographs of slab gels after SDS-PAGE illustrating protein samples isolated by different procedures.

In column A of FIG. 3, the protein sample was the total lysate of surface radioiodinated RBL-2H3 cells.

In column B, the total lysate was first passed through a cromolyn-BSA-Sepharose column, such as that produced by the procedure of Example 13, eluted with 20 mM cromolyn and 10 mM dithiothreitol (DTT) in buffer X (0.2 M borate, 0.16 M NaCl, 2 mM Ca$^{2+}$, 0.5% Triton X-100, 0.15 soy-bean lipids pH 7.4).

The protein sample used to obtain the results shown in column C was that eluted from a column containing glutamate-BSA-Sepharose. This matrix was prepared in the same manner as the cromolyn-BSA-Sepharose matrix except that in the production of the cromolyn-BSA conjugate, an equimolar quantity of sodium glutamate was substituted for cromolyn to provide a control. The glutamate-BSA-Sepharose column was eluted with 20 mM cromolyn and 10 mM DTT in buffer X.

The protein sample used to obtain the results shown in column D of FIG. 3 was the eluate of the lysate of surface radioiodinated RBL-2H3 cells passed through a cromolyn-BSA-DNP-MOPC 315-Sepharose column (prepared in a manner analogous to that described in Example 16), eluted with 5 mM Ne-DNP-lysine in buffer X.

In all of columns A-D of FIG. 3, 10-15% polyacrylamide gradient gel was used and the samples were reduced with mercaptoethanol.

In column E, an unreduced sample was first passed though a cromolyn-BSA-DNP-MOPC 315-Sepharose column and eluted with 5 mM Ne-DNP-lysine in buffer X using 7-10% polyacrylamide gradient gel.

EXAMPLE 19

Figure 4A:
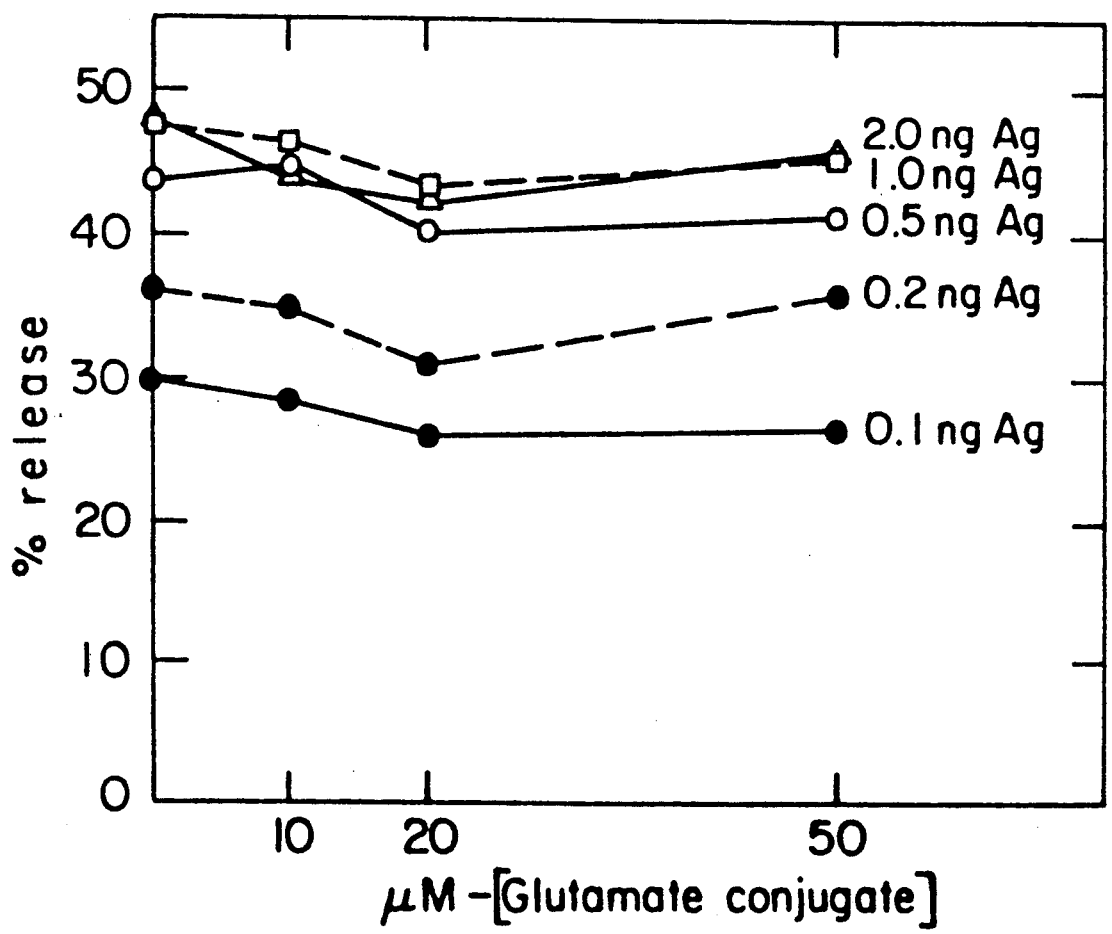
FIGS. 4A to 4C illustrate the high inhibition capacity of cromolyn conjugates vis-a-vis the glutamate-conjugate control.
Figure 4B:
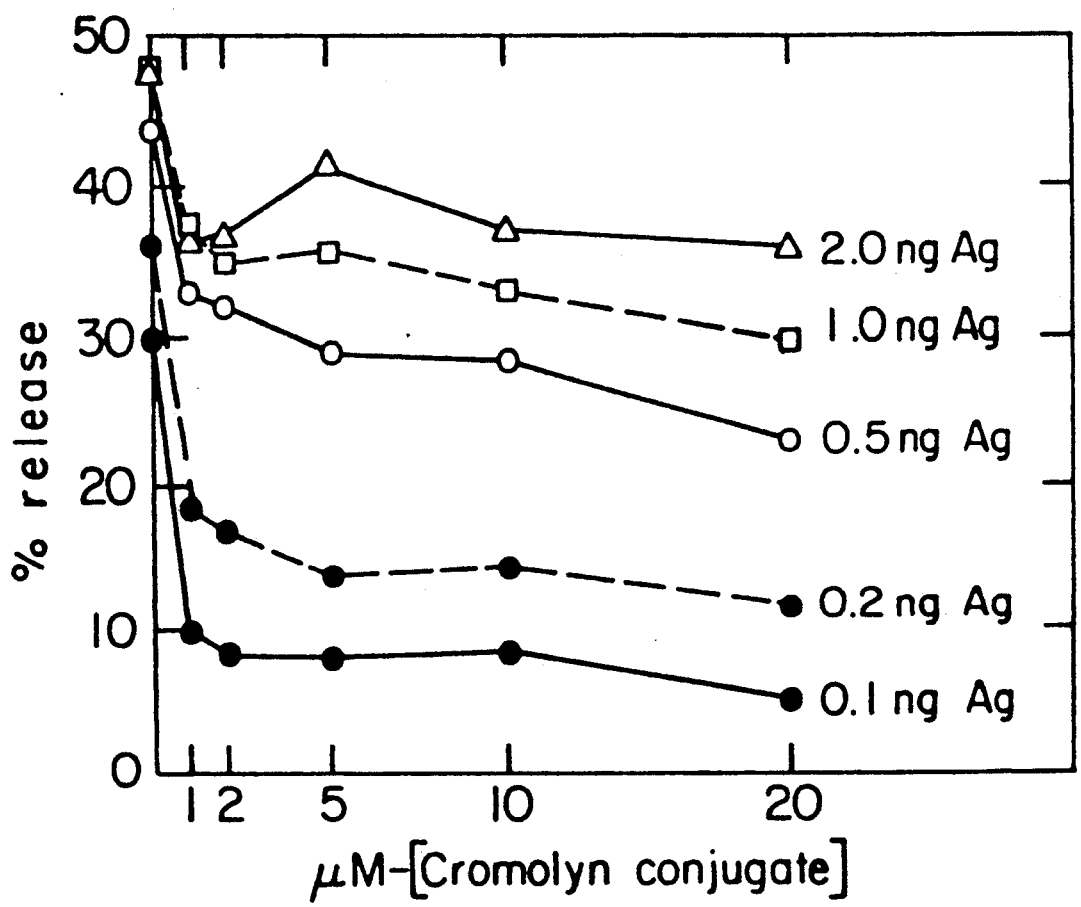
Figure 4C:
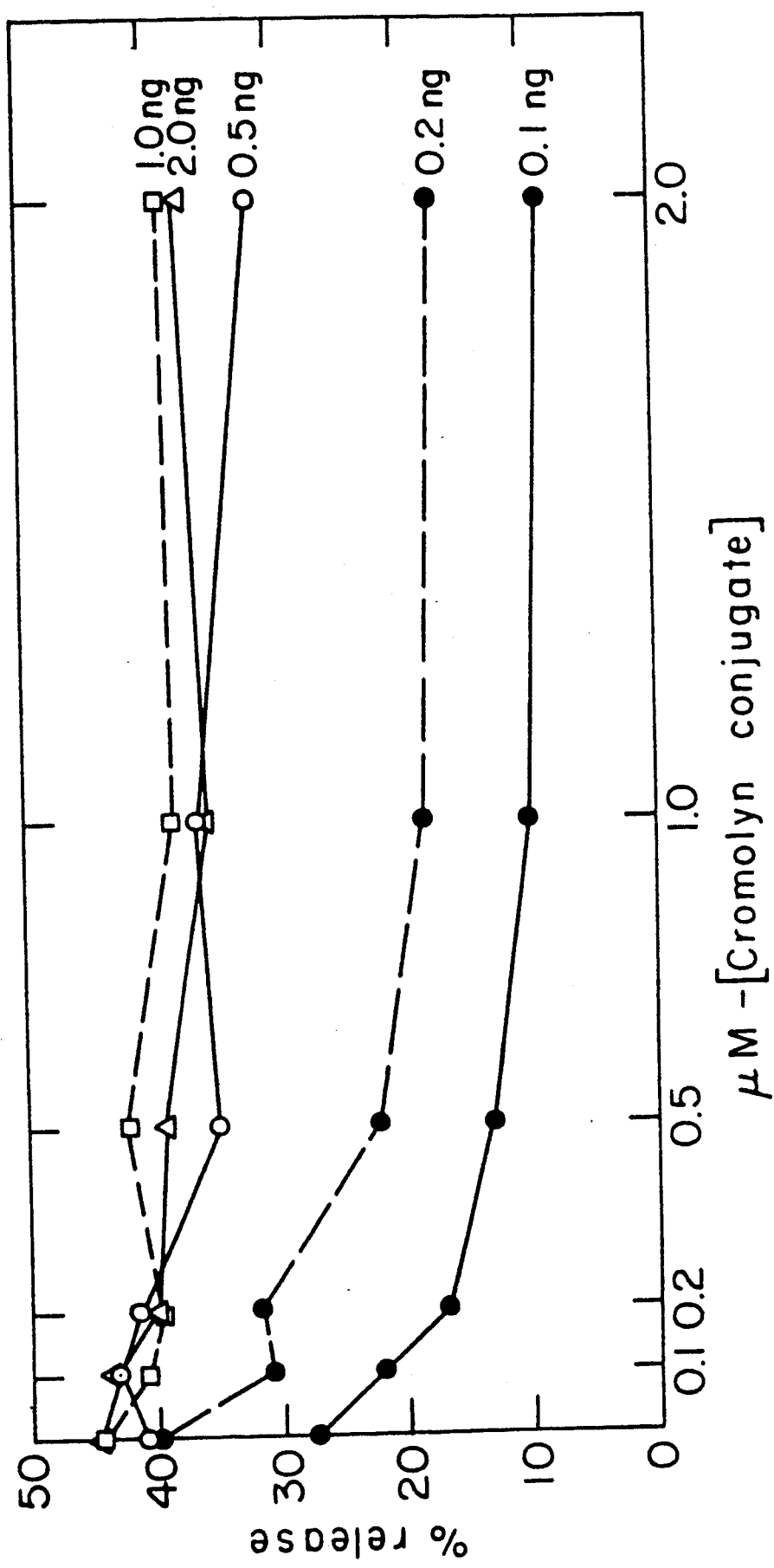

Inhibition of the antigen-induced degranulation of RBL-2H3 cells by the conjugate of cromolyn with BSA To establish that the pharmacologically active portion of the cromolyn molecule is not effected by modification of the residue on the 2-carbon of the propane link, degranulation studies were conducted using the conjugate of aminocromolyn with BSA. Degranulation was monitored by a slight modification of the procedure for measuring [$^3$H]serotonin release described by Taurog et al. (*J. Immunol.*, 119, 1757-1761 (1977)). Each assay was carried out with 10$^5$ cells. The cells were sensitized with a monoclonal DNP-specific IgE and triggered for degranulation by addition of different amounts of DNP$_{11}$-BSA. The release is expressed as percentage of total cell-incorporated [$^3$H]serotonin. All measurements were done in triplicates, and the points plotted in the graphs of FIGS. 4A-4C represent their average values. In FIG. 4A a glutamate-BSA control was used. It can be seen that there is substantially no effect on degranulation. FIGS. 4B and 4C use the cromolyn-BSA conjugate and substantial effect can be seen.

EXAMPLE 20

Purification of CBP (reduced form) on lectin affinity columns

Two 1 ml aliquots of a solution containing the cromolyn binding protein along with DNP$_8$-BSA-cro$_{10}$ in buffer I (see example 15) containing 10 mM beta-mercaptoethanol were passed over two lectin affinity columns which contained either 1 ml wheat germ agglutinin agarose (3 mg WGA per ml matrix) or 1 ml concanavalin A agarose (5 mg ConA per ml matrix) equilibrated in buffer I at 4° C. The results are shown in FIG. 5. Lines 2 and 3 represent effluent only. The columns were washed in the cold with buffer I, then they were eluted at 25° C. with 5% N-acetylglucosamine in buffer I (WGA-column) or 5% alpha-methylmannopyranoside in buffer I (ConA). Lines E1-E6 represent the eluate from these columns. The eluted matrix was later boiled in reducing SDS-PAGE-sample buffer (0.625 M Tris-HCl pH 8.0, 3% SDS, 10% glycerol, 0.25 M beta-mercaptoethanol, 0.5 mg/ml bromophenol blue) and the extract was also analyzed by SDS-PAGE in order to detect uneluted protein. The results are shown in line B.

EXAMPLE 21

Preparation of Hetero-Antibodies Against CBP

Rabbits are immunized by multisite intradermal injections of 0.5 mg per rabbit of the cromolyn binding protein purified on the BSA-(ga)-cro$_{10}$-Sepharose column and further purified on a WGA-agarose column to substantial purity, in complete Freund's adjuvant. Rabbits were boosted three weeks later with 0.4 mg purified protein and bled 4 and 5 weeks after immunization. The serum was separated and stored frozen.

EXAMPLE 22

Monoclonal Antibodies against purified CBP

Monoclonal antibodies against the purified cromolyn binding protein are obtained utilizing commonly used techniques (Galtre, G. et al, *Nature*, 266, 550 (1977)).

Spleen cells of C57B1/6J (female) mice, previously immunized with the substantially pure cromolyn binding protein (50 ug/mouse), are fused to the NSl-Ag4/1 myeloma line, in the presence of polyethylene glycol 1500. Hybrid clones are screened for Ig secretion and inhibition of cromolyn binding to RBL-2H3 cells. Positive hybrid cultures are cloned in soft agar. The clones are cultured and screened once more for Ig secretion and inhibition of cromolyn binding. Positive clones are maintained and the antibodies produced thereby are purified and maintained.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

We claim:

1. A method of purifying cromolyn binding protein, comprising:
    preparing a chromatography column packed with an insoluble matrix having bound thereto a cromolyn derivative of the general formula

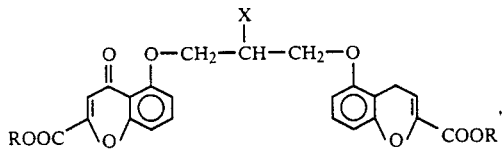

(I)

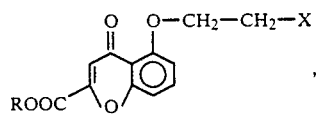

(II)

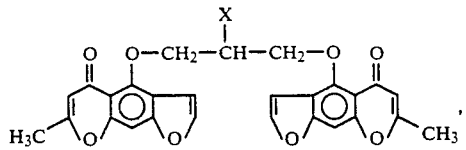

(III)

or

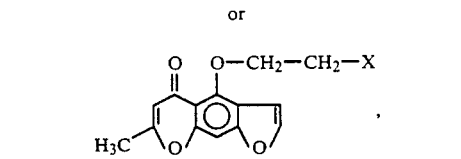

(IV)

wherein R is hydrogen or $C_{1-5}$ alkyl and X is amino or an amino derivative;
    lysing cells in which cromolyn binding protein is naturally occurring or solubilizing the plasma membrane of said cells;
    separating any cromolyn binding protein contained in said lysed cells or solubilized membranes from the non-desired contaminants by passing said lysed cells or solubilized membranes through said column, whereby any cromolyn binding protein is retained on the column while non-desired contaminants pass through; and
    eluting the cromolyn binding protein bound to said immobilized cromolyn derivative.

2. A method in accordance with claim 1 and further including the step of further purifying the cromolyn binding protein eluted from said column by subjecting said eluate to SDS-polyacrylamide gel electrophoresis.

3. A method in accordance with claim 1 and further including the step of further purifying the cromolyn binding protein eluted from said column by incubating said eluate on a lectin-agarose conjugate and eluting the cromolyn binding protein which binds to said conjugate.

4. A method in accordance with claim 3 wherein said lectin is wheat germ agglutinin or concanavalin A.

5. An essentially pure protein consisting essentially of cromolyn binding protein in intact, unreduced form, said protein being glycosylated and having an apparent molecular mass of 110,000 as determined by SDS-polyacrylamide gel electrophoresis analysis, and wherein the reduced form of said protein has the following amino acid composition:

| Amino Acid | % w/w | % mol/mol |
|---|---|---|
| Asp | 9.32 | 8.78 |
| Thr | 4.20 | 4.53 |
| Ser | 5.99 | 7.43 |
| Glu | 15.37 | 12.89 |
| Gly | 6.17 | 11.71 |
| Ala | 5.31 | 8.08 |
| Val | 8.40 | 9.19 |
| Met | 0.99 | 0.78 |
| Ile | 6.23 | 5.96 |
| Leu | 7.47 | 7.15 |
| Tyr | 1.85 | 1.24 |
| Phe | 3.89 | 2.86 |
| His | 7.96 | 6.28 |
| Lys | 8.95 | 7.78 |
| Arg | 8.02 | 5.57. |

6. An essentially pure protein consisting essentially of cromolyn binding protein in reduced form, said protein being glycosylated, having an apparent molecular mass of 50,000 as determined by SDS-polyacrylamide gel electrophoresis analysis, and having the following amino acid composition:

| Amino Acid | % w/w | % mol/mol |
|---|---|---|
| Asp | 9.32 | 8.78 |
| Thr | 4.20 | 4.53 |
| Ser | 5.99 | 7.43 |
| Glu | 15.37 | 12.89 |
| Gly | 6.17 | 11.71 |
| Ala | 5.31 | 8.08 |
| Val | 8.40 | 9.19 |
| Met | 0.99 | 0.78 |
| Ile | 6.23 | 5.96 |
| Leu | 7.47 | 7.15 |
| Tyr | 1.85 | 1.24 |
| Phe | 3.89 | 2.86 |
| His | 7.96 | 6.28 |
| Lys | 8.95 | 7.78 |
| Arg | 8.02 | 5.57. |

7. The essentially pure protein consisting essentially of cromolyn binding protein produced by the process of claim 1, which, in intact unreduced form, is glycosylated and has an apparent molecular mass of 100,000 as determined by SDS-polyacrylamide gel electrophoresis analysis.

8. The essentially pure protein consisting essentially of cromolyn binding protein produced by the process of claim 2, which, in intact unreduced form is glycosylated and has an apparent molecular mass of 110,000 as determined by SDS-polyacrylamide gel electrophoresis analysis.

9. The essentially pure protein consisting essentially of cromolyn binding protein produced by the process of claim 3, which, in intact unreduced form, is glycosylated and has an apparent molecular mass of 110,000 as determined by SDS-polyacrylamide gel electrophoresis analysis.

10. The essentially pure protein consisting essentially of cromolyn binding protein produced by the process of claim 4, which, in intact unreduced form, is glycosylated and has an apparent molecular mass of 110,000 as determined by SDS-polyacrylamide gel electrophoresis analysis.

* * * * *